United States Patent [19]

Cue

[11] 4,100,284  
[45] Jul. 11, 1978

[54] 1,4-DIOXO- AND 4-OXOQUINOXALINE-2-CARBOXALDEHYDE SULFONYLHYDRAZONES AND CERTAIN DERIVATIVES THEREOF

[75] Inventor: Berkeley W. Cue, Groton, Conn.

[73] Assignee: Pfizer Inc., New York, N.Y.

[21] Appl. No.: 760,271

[22] Filed: Jan. 18, 1977

[51] Int. Cl.² .................................. C07D 239/76
[52] U.S. Cl. ..................... 424/250; 542/418; 544/353; 544/355
[58] Field of Search ............... 424/250; 260/250 Q, 260/250 QN, 240 G; 542/416

[56] References Cited

U.S. PATENT DOCUMENTS

| | | | |
|---|---|---|---|
| 3,371,090 | 2/1968 | Johnston | 260/240 G |
| 3,493,572 | 2/1970 | Johnston | 260/240 G |
| 3,819,616 | 6/1974 | Seng et al. | 260/240 G |
| 3,839,326 | 10/1974 | Seng et al. | 260/250 QN |
| 3,928,608 | 12/1975 | Cox et al. | 260/250 Q |
| 3,931,174 | 1/1976 | McFarland | 424/250 |

OTHER PUBLICATIONS

Sartorelli et al., J. Med. Chem., 19 (1976), pp. 830–833.

*Primary Examiner*—Arthur P. Demers
*Attorney, Agent, or Firm*—Connolly and Hutz

[57] ABSTRACT

The invention relates to novel chemical compounds which have useful antibacterial properties and are also of value in promoting animal growth and improving animal feed efficiency. More specifically, these new chemical compounds are certain sulfonylhydrazones of 1,4-dioxoquinoxaline-2-carboxaldehyde, 4-oxoquinoxaline-2-carboxaldehyde and certain derivatives thereof of formula (I):

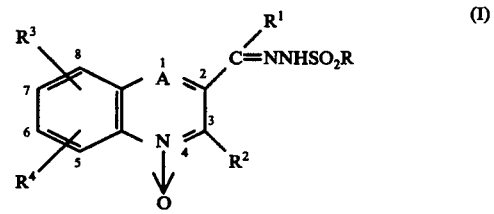

wherein A is N or N → O; R is a member selected from the group consisting of alkyl having from one to five carbon atoms, trifluoromethyl, phenyl, npahthyl, benzyl, styryl and phenyl substituted by up to two members selected from the group consisting of Cl, F, Br, $CH_3$, $CH_3O$ and $NO_2$; $R^1$ is hydrogen or methyl; $R^2$ is hydrogen or methyl; $R^3$ is a 6- or 7-position substituent and is selected from the group H, Cl, $CH_3$, $CH_3O$, $SO_2NH_2$, $SO_2NHCH_3$ and $SO_2N(CH_3)_2$; $R^4$ is a 7- or 6-position substituent and is selected from the group H, Cl and $CH_3$; with the proviso that when $R^4$ is Cl or $CH_3$, $R^3$ and $R^4$ are the same.

14 Claims, No Drawings

1,4-DIOXO- AND 4-OXOQUINOXALINE-2-CARBOXALDEHYDE SULFONYLHYDRAZONES AND CERTAIN DERIVATIVES THEREOF

BACKGROUND OF THE INVENTION

1. Field of the Invention

This invention relates to certain novel sulfonylhydrazones of 1,4-dioxoquinoxaline-2-carboxaldehyde, 4-oxoquinoxaline-2-carboxaldehyde, certain derivatives thereof and to their use as antibacterial agents and for promoting growth and improving feed efficiency in animals.

2. Description of the Prior Art

Schiff bases derived from 2-formylquinoxaline-1,4-dioxides and carbonyl-containing hydrazine derivatives are well known compounds, some of which are useful as antibacterial agents and are valuable as growth promoting agents in animals. U.S. Pat. No. 3,371,090 discloses Schiff bases of the formula:

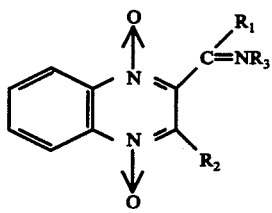

wherein $R_1$ and $R_2$ are each hydrogen and lower alkyl; $R_3$ is selected from the group consisting of $NHCSNH_2$, $NHC(NH)NH_2$, $NHR_4$, $NHCOOR_5$, $NHCOR_6$, $OR_7$,

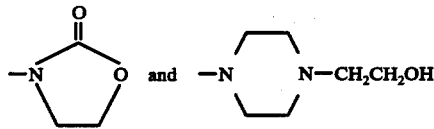

wherein $R_4$ is lower alkyl, benzyl or hydroxyalkyl having from 2 to 4 carbon atoms; $R_5$ is lower alkyl, hydroxyalkyl having from 2 to 4 carbon atoms or haloalkyl having from 2 to 4 carbon atoms; $R_6$ is lower alkyl or phenyl; and $R_7$ is lower alkyl. Methods for promoting growth and improving feed efficiency of animals and animal feed compositions employing these compounds are disclosed in U.S. Pat. No. 3,433,871.

Arylsulfonylhydrazones of formylpyridine N-oxides, 2-formylquinoline N-oxide phenylsulfonylhydrazone and the corresponding 1-formylisoquinoline compound were recently reported by Sartorelli et al., *J. Med. Chem.*, 19, 830 (1976). The 2-formylpyridine-N-oxide arylsulfonylhydrazones were found to have tumor inhibiting properties. However, replacement of the pyridine ring with benzene, quinoline or isoquinoline resulted in loss of activity; movement of the formylsulfonylhydrazone side chain from the 2 to the 3 or 4 position of the pyridine-N-oxide also produced inactive compounds; and replacement of the $SO_2$ by $C=O$ resulted in complete loss of activity.

SUMMARY OF THE INVENTION

It is an object of the invention to provide novel sulfonylhydrazones of 1,4-dioxoquinoxaline-2-carboxaldehyde, 4-oxoquinoxaline-2-carboxaldehyde and certain derivatives thereof of the formula (I):

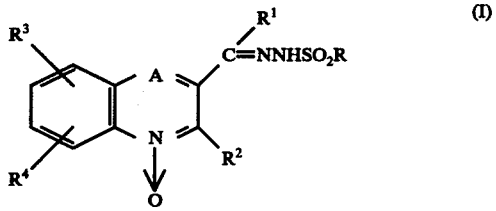

wherein A is N or N → O; R is a member selected from the group consisting of alkyl having from one to five carbon atoms, trifluoromethyl, phenyl, naphthyl, benzyl, styryl and phenyl substituted by up to two members selected from the group consisting of Cl, F, Br, $CH_3$, $CH_3O$ and $NO_2$; $R^1$ is hydrogen or methyl; $R^2$ is hydrogen or methyl; $R^3$ is a 6- or 7-position substituent and is selected from the group consisting of H, Cl, $CH_3$, $CH_3O$, $SO_2NH_2$, $SO_2NHCH_3$ and $SO_2N(CH_3)_2$; $R^4$ is a 7- or 6-position substituent and is selected from the group consisting of H, Cl and $CH_3$; with the proviso that when $R^4$ is Cl or $CH_3$, $R^3$ and $R^4$ are the same.

Especially preferred compounds of formula (I) are those wherein $R^1$, $R^2$, $R^3$ and $R^4$ are each hydrogen. Especially preferred values of R are 4-methylphenyl, 4-methoxyphenyl, 4-fluorophenyl, phenyl and methyl.

Another object of the invention is to provide a method for promoting growth and improving feed efficiency of animals which comprises feeding said animals a growth promoting amount of a compound of formula (I).

A further object of the invention is to provide an animal feed composition which comprises a nutritionally balanced feed containing from about 5 g. to about 200 g. per ton of feed of a compound of formula (I).

DETAILED DESCRIPTION OF THE INVENTION

The valuable compounds of this invention are prepared by condensing the appropriate sulfonyl hydrazide of the formula $RSO_2NHNH_2$ in which R is defined above, with the appropriate 1,4-dioxo- or 4-oxoquinoxaline of the formula (II):

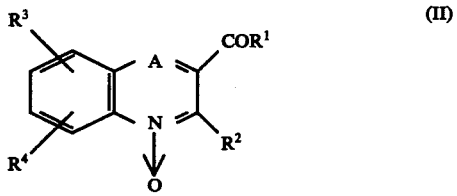

wherein A, $R^1$, $R^2$, $R^3$ and $R^4$ are as previously defined. Approximately equimolar amounts of the reactants are reacted in a suitable reaction inert solvent at a temperature of from about room temperature to the reflux temperature of the solvent, temperatures of from about 25° to 100° C. are especially preferred. Suitable solvents are those which will serve to dissolve the reactants and will not adversely interact with either the starting materials or the product. Examples of such solvents are acetic acid, ethyl ether and the lower alkanols such as methanol, ethanol, isopropanol and the like. Methanol is especially preferred.

The time couse of the reaction varies according to factors such as the reactivity of the particular reagents employed, the concentration of the reagents, the reaction solvent and the reaction temperature. As will be appreciated by one skilled in the art, the reaction proceeds faster at higher temperatures are relatively short reaction times are required to reach substantial completion. Conversely, at lower temperatures the reaction proceeds more slowly, thus requiring longer reaction times to achieve a good yield of the desired product. Ordinarily, however, reaction time of from about one to four hours give satisfactory results.

The products ordinarily precipitated from the reaction mixture are collected by suitable means such as, for example, by filtration, and dried. In those cases where the product does not precipitate, the solvent can be removed by evaporation or the product precipitated by addition of a non-solvent such as, for example, hexane, heptane or benzene. The products may be further purified, if desired, by recrystallization from solvents such as, for example, methanol, ethanol or aqueous N,N-dimethylformamide.

An alternate method for preparing the valuable sulfonylhydrazones of formula (I) comprises reacting an intermediate hydrazone of formula (III):

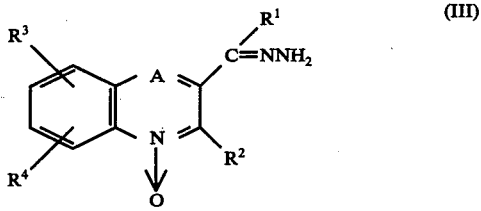

wherein A, $R^1$, $R^2$, $R^3$ and $R^4$ are as previously defined, with a sulfonyl chloride, $RSO_2Cl$, wherein R is as defined above, or the corresponding solfonyl bromide. The reaction is carried out in the presence of a reaction inert solvent and preferably in the presence of a tertiary amine which acts as an acid acceptor, i.e., combines with the hydrogen halide produced in the reaction to form an acid addition salt which is often insoluble in the reaction inert solvent and is thus removed from the reaction by precipitation. Examples of suitable reaction inert solvents for this reaction are ethers such as, for example, ethyl ether, isopropyl ether, 1,2-dimethoxy ethane, diethyleneglycol dimethyl ether and tetrahydrofuran, benzene, toluene and acetonitrile. Especially preferred as solvent are ethyl ether and tetrahydrofuran. The preferred tertiary amine is triethylamine for reasons of convenience and economy. While the reaction may be carried out over a wide range of temperatures with satisfactory results, a temperature of from about 10° to 70° C. is preferred. Ordinarily, the reaction is substantially complete in 1 hour or less. The product of formula (I) is isolated by standard methods such as, for example, filtering to remove precipitated salt, and evaporation of the filtrate. The residual product may be further purified, if desired, for example, by recrystallization as described above.

The intermediate hydrazones of formula (III) are prepared from the appropriate compound of formula (II) and hydrazine or hydrazne hydrate by methods well known in the art for forming hydrazones, see for example, Schonberg et al., *J. Am. Chem. Soc.*, 79, 6020 (1957).

Another method for preparing the valuable sulfonylhydrazones of formula (I) comprises reacting an acetal or ketal of the formula (IV):

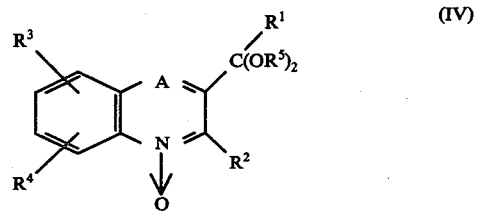

wherein A, $R^1$, $R^2$, $R^3$ and $R^4$ are as previously defined and $R^5$ is alkyl having up to four carbon atoms with at least an equimolar amount of a sulfonyl hydrazide of the formula $RSO_2NHNH_2$ in which R is as defined above. Said reaction is carried out in a reaction inert solvent at a temperature of from about 30° to 200° C. for up to 24 hours and in the presence of at least a catalytic amount of a strong acid. A similar process has been disclosed in U.S. Pat. No. 3,493,572 for preparing the Schiff bases derived from 2-formylquinoxaline-1,4-dioxides and carbonyl-containing hydrazine derivatives discussed above under Description of the Prior Art.

Preferred solvents for the latter method for preparing compound (I) includes hydrocarbon solvents such as benzene, toluene and xylene and alcoholic solvents such as methanol and ethanol, and ethyl acetate. For purposes of the invention the term "strong acid" includes any species which allows protonation of the acetal or ketal of formula (IV) with the ability to cause its reversion to the free aldehyde or ketone. Examples of such strong acids are hydrochloric and sulfuric acids. The acetal or ketal starting material of formula (IV) are readily prepared from the corresponding aldehydes or ketones of formula (II) by well known procedures. Alternatively, those of formula (IV) wherein $R^1$ and $R^2$ are each hydrogen and A is N → O may be prepared from the appropriate benzofuroxan and a pyruvaldehyde alkyl acetal, preferably the methyl acetal, by the procedure of British Pat. No. 1,215,815.

The starting sulfonylhydrazides (also known as sulfonylhydrazines or sulfonhydrazides) are either commercially available or are readily prepared from the appropriate sulfonyl halides, such as the commercially available sulfonyl chlorides and hydrazine hydrate by the procedure described in *Organic Syntheses*, 40, 93 (1960) for the preparation of p-toluenesulfonylhydrazide.

The requisite 1,4-dioxoquinoxaline-2-carboxaldehyde starting materials of the formula (II) wherein A is N → O, $R^1$ and $R^2$ are each hydrogen and $R^3$ and $R^4$ are as previously defined, are prepared by reacting the appropriate benzofuroxan with a dialkyl acetal of pyruvaldehyde and, preferably, with pyruvaldehyde dimethylacetal in a reaction inert solvent such as acetonitrile in the presence of a base such as pyrrolidine then hydrolysis of the resulting acetal according to the process of British Pat. No. 1,215,815.

The starting 3-methyl-1,4-dioxoquinoxaline-2-carboxaldehydes of formula (II) wherein A is N → O, $R^1$ is hydrogen, $R^2$ is methyl and $R^3$ and $R^4$ are as previously defined, are prepared from the corresponding 2-hydroxymethyl-3-methyl-1,4-dioxoquinoxalines by a sequence of steps comprising: (a) reaction with hydrobromic acid to form a 2-bromomethyl-3-methyl-1,4-dioxoquinoxaline; and (b) oxidation of the bromo derivative with dimethylsulfoxide to produce the desired 2-carboxaldehyde compound. The 2-hydroxymethyl-3-methyl -1,4-dioxoquinoxalines are prepared by reacting the appropriate benzofuroxan with 4-hydroxy-2-butanone in a reaction inert solvent, e.g., N,N-dimethylformamide, in the presence of pyrrolidine according to the procedure of British Pat. No. 1,215,815.

The 2-methylcarbonyl-1,4-dioxoquinoxalines of formula (II) wherein A is N → O, $R^1$ is methyl, $R^2$ is hydrogen or methyl and $R^3$ and $R^4$ are as previously defined are similarly prepared from the appropriate benzofuroxan and biacetyl, for the case wherein $R^2$ is hydrogen, or pentane-2,4-dione, for the case wherein $R^2$ is methyl. The reaction is carried out in the presence of a reaction inert solvent in the presence of a catalytic amount of a base such as sodium hydroxide.

The starting 4-oxoquinoxaline-2-carbonyl compounds of formula (II) wherein A is N are prepared from 1,4-dioxoquinoxalines. The 4-oxoquinoxaline-2-carboxaldehydes of formula (II) wherein A is N, $R^1$ and $R^2$ are each hydrogen and $R^3$ and $R^4$ are as previously defined, are prepared from the corresponding 2-hydroxymethyl-1,4-dioxoquinoxalines by heating them in the presence of a strong acid such as concentrated hydrochloric acid, concentrated sulfuric acid or concentrated phosphoric acid. The reaction is carried out at a temperature of from about 25° to 125° C., and preferably from about 70° to 110° C. for periods of from about 15 minutes to 4 hours. Of course, the reaction rate will vary with temperature according to the well-known laws of thermodynamics, i.e. shorter times will be required at higher temperatures and longer times at lower temperatures. The desired 4-oxoquinoxalines precipitate from the cooled reaction mixture and are isolated and purified, if desired, by standard techniques well known in the art. The requisite 2-hydroxymethyl-1,4-dioxoquinoxalines are prepared from the corresponding 2-carboxaldehydes by reduction with a metal hydride such as sodium borohydride or alternatively, by treatment with a tri(lower)alkyl phosphite. By the term tri(lower)alkyl phosphite is meant a trialkyl phosphite having from one to four carbon atoms in each of the alkyl groups. Trimethyl phosphite is preferred for reasons of convenience and economy. The process is carried out with approximately equimolar amounts of the appropriate 1,4-dioxoquinoxaline-2-carboxaldehyde and tri(lower)alkyl phosphite in the presence of a reaction inert organic solvent such as one of the lower alkanols, for example, methanol, ethanol, n-propanol or isopropanol; or N,N-dimethylformamide. The mixture is heated at a temperature of from about 50° to 160° C. for periods of from a few minutes to a few hours. Ordinarily, when carried out at the reflux of 1-propanol, the reaction is substantially complete in about one-half hour. Upon cooling, the product precipitates and is isolated by standard methods.

The 3-methyl-4-oxoquinoxaline-2-carboxaldehyde starting materials of formula (II) wherein A is N, $R^1$ is hydrogen, $R^2$ is methyl and $R^3$ and $R^4$ are as previously defined, are prepared from the corresponding 2-hydroxymethyl-1,4-dioxoquinoxalines by treatment with strong acid by the same process described above for the corresponding compounds of formula (II) wherein $R^2$ is hydrogen.

The 4-oxoquinoxaline intermediates of formula (II) wherein A is N, $R^1$ is methyl, $R^2$ is hydrogen or methyl and $R^3$ and $R^4$ are as defined above, are prepared from the corresponding 2-methylcarbonyl-1,4-dioxoquinoxalines. The latter compounds are reacted with a tri(lower)alkyl phosphite, preferably trimethyl phosphite, in the presence of a reaction inert solvent. Examples of such solvents are the lower alkanols such as methanol, ethanol, n-propanol and isopropanol; and N,N-dimethylformamide. The preferred solvent is n-propanol. The reaction is carried out by reacting approximately equimolar amount of the appropriate 2-methylcarbonyl-1,4-dioxoquinoxaline and tri(lower)alkyl phosphite at a temperature of from about 50° to 150° C. and preferably about 80° to 120° C. The time required to reach substantial completion, of course, will vary with temperature as well as other factors such as, for example, the precise nature of the reactants and solvent. Ordinarily, however, reaction times of from about 1 to 10 hours will be sufficient. The desired product often precipitates from solution upon cooling of the reaction mixture and is then readily isolated by standard methods. If the product does not precipitate, it can be isolated by removal of solvent, e.g., by evaporation, or alternatively the product can be precipitated by addition of a non-solvent such as hexane or benzene and the product then isolated by standard techniques.

The valuable products of this invention are remarkably effective in treating a wide variety of pathogenic microorganisms. They are, therefore, useful as industrial antimicrobials, for example, in water treatment, slime control, paint preservation and wood preservation as well as for topical application purposes as disinfectants.

For in vitro use, e.g., for topical application, it will often be convenient to compound the selected product with a non-toxic carrier such as vegetable or mineral oil or an emollient cream. Similarly, they may be dissolved or dispersed in liquid carriers or solvents such as water, alcohol, glycols or mixtures thereof or other non-toxic inert media, that is, media which have no harmful effect on the active ingredient. For such purposes, it will generally be acceptable to employ concentrations of active ingredients of from about 0.01 percent to about 10 percent by weight based on total composition.

Further, many of the compounds described herein exhibit broad spectrum activity, that is, activity against both gram-negative and gram-positive bacteria, such as *Escherichia coli, Salmonella cholerasuis, Staphylococcus aureus, Streptococcus pyrogenes* and *Pasteurella multocida*. This is in contrast to the usual gram-negative activity of quinoxaline-di-N-oxides. Additionally, many of them are active in vivo and are especially useful as animal growth promotants, especially for swine and poultry. Especially, preferred in view of their antibacterial activity are those compounds of formula (I) wherein A is a nitrogen atom, $R^1$, $R^2$, $R^3$ and $R^4$ are each hydrogen and R is $R^5$ where $R^5$ is a member selected from the group consisting of methylphenyl and methoxyphenyl and those compounds of formula (I) wherein A is N→O, $R^1$, $R^2$, $R^3$ and $R^4$ are each hydrogen and R is $R^6$ where $R^6$ is a member selected from the group consisting of alkyl having from one to five carbon atoms, phenyl, methylphenyl and fluorophenyl. Particularly preferred because of their in vivo activity are 4-oxoquinoxaline-2-carboxaldehyde p-toluenesulfonylhydrazone and 1,4-dioxoquinoxaline-2-carboxaldehyde p-toluenesulfonylhydrazone.

When used in vivo for such purposes, these novel compounds can be administered orally or parenterally, e.g., by subcutaneous or intramuscular injection, at a dosage of from about 1 mg./kg. to about 100 mg./kg. of body weight. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide, and other nonaqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptably inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

Other methods include mixing with animal feeds, the preparation of feed concentrates and supplements and dilute solutions or suspensions, e.g., a 0.1 percent solution, for drinking purposes. The addition of a low level of oneor more of the herein described active compounds of formula (I) to the diet of healthy animals, both ruminant and non-ruminant, such that these animals receive the product over an extended period of time, at a level of from about 1 mg./kg. to about 100 mg./kg. of body weight per day, especially over a major portion of their active growth period, results in an acceleration of the rate of growth and improves feed efficiency (the number of pounds of feed required to produce a pound gain in weight). Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed.

The herein described feed compositions have been found to be particularly valuable and outstanding in the case of swine. In some instances, the degree of response may vary with respect to the sex of the animals. The products may, of course, be admininstered in one component of the feed or they may be blended uniformly throughout a mixed feed; alternatively, as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of the compounds of formula (I) described above. Some of the carious components are commonly grains such as ground grain and grain by-products; animal protein substances, such as meat and fish by-products; vitaminaceous mixtures; e.g., vitamin A and D mixtures, riboflavin supplements and other vitamine B complexes; and bone meal, limestone and other inorganic compunds to provide minerals.

The relative proportions of the present compounds in feeds and feed concentrates may vary somewhat, depending upon the compound, the feed with which they are employed and the animal consuming the same. These substances are advantageously combined in such relative proportions with edible carriers as to provide pre-mixes or concentrates which may readily be blended with standard nutritionally balanced feeds or which may be used themselves as an adjunct to normal feedings.

In the preparation of concentrates to a wide variety of carriers, including the following: soybean oil meal, corn gluten meal, cotton seed oil meal, sunflower seed meal, linseed oil meal, cornmeal, limestone and corncob meal can be employed. The carrier facilitates uniform distribution of the active materials in the finished feed with which the concentrate is blended. The concentrate may be surface coated, if desired, with various proteinaceous materials or edible waxes, such as zein, gelatin, microcrystalline wax and the like to provide a protective film which seals in the active ingredients. It will be appreciated that the proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e. premixes, suitable for blending by feed manufacturers to produce finished feeds or concentrates of lower potency, the drug content may range from about 0.1 g. to 50 g. per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.1 to 10 g. per pound of supplement. A particularly useful concentrate is provided by blending 2 g. of drug with 1 pound of limestone or 1 pound of limestone-soybean oil meal (1:1). Other dietary supplements, such as vitamins, minerals, etc. may be added to the concentrates in the appropriate circumstances.

The concentrates described may also be added to animal feeds to produce a nutritionally balanced, finished feed containing from about 5 to about 200 g. of the herein described compounds per ton of finished feed. In the case of ruminants, the finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa hay or meal, cracked corn, whole oats, soybean oil meal, corn silage, ground corn cobs, wheat bran and dried molasses. Bone meal, limestone, iodized salt and trace minerals are frequently added to supply the necessary minerals and urea to provide additional nitrogen.

As is well known to those skilled in the art, the type of diets are extremely variable depending upon the purpose, type of feeding operation, species, etc. Specific diets for various purposes are listed by Morrison in the Appendix of "Feeds and Feeding", the Morrison Publishing Company, Clinton, Iowa, 1959.

In the case of non-ruminant animals, such as hogs, a suitable feed may contain from about 50 to 80 percent of grains, 3 to 10 percent animal protein, 5 to 30 percent vegetable protein, 2 to 4 percent of minerals, together with supplementary vitaminaceous sources.

The in vitro antibacterial activity of the compounds of the invention can be demonstrated by the conventional two-fold serial dilution technique in Brain-Heart Infusion broth (Difco). The broth is inoculated with bacteria, and with the test compound of formula (I), and then it is incubated overnight under anaerobic conditions. On the next day, the test is read visually. The minimum inhibitory concentration (MIC) of test compound is the lowest concentration which prevents turbidity, i.e., which prevents growth of the microorganism. In vitro activities of a number of compounds of the instant invention are shown in Table I.

The compounds of formula (I) also show antibacterial activity in vivo. In determining such activity, the test compound is administered to mice which have been infected by intraperitoneal injection of a lethal inoculum of pathogenic bacteria. The test compound is administered using a multiple dosing regimen, and using either the oral (PO) or the subcutaneous (SC) route. The inoculum of bacteria varies from one to about ten times the amount needed to kill 100% of the mice, under the conditions of the test. At the end of the test, the activity of a compound is assessed by counting the number of survivors among the treated animals. Results are also given in Table I, wherein the ability of the compound to protect mice against a lethal challenge of *Salmonella cholerasuis* is presented.

tone to afford 0.57 g. (63%) of the title compound, M.P. 175°–176° C. $^1$H-nmr (CF$_3$CO$_2$D) ppm δ: 7.6–8.4 (4, m, benzenoid H), 8.87 (1, s, H at 3-position), 9.60 (1, s, CHO). The mass spectrum showed a molecular ion at M/e 174.

B. When the above procedure is repeated, but employing the appropriate starting material in place of 2-hydroxymethyl-1,4-dioxoquinoxaline in each case, the following compounds are obtained in like manner.

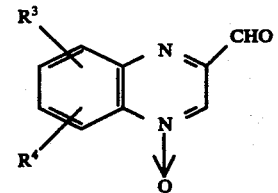

| $R^3$ | $R^4$ |
|---|---|
| Cl | H |
| CH$_3$ | H |
| OCH$_3$ | H |
| SO$_2$NH$_2$ | H |
| SO$_2$NHCH$_3$ | H |
| SO$_2$N(CH$_3$)$_2$ | H |
| Cl | Cl |
| CH$_3$ | CH$_3$ |

EXAMPLE 2

2-Methylcarbonyl-3-methyl-4-oxoquinoxaline

TABLE 1

IN VITRO AND IN VIVO ANTIBACTERIAL DATA, MIC (mcg./ml.)

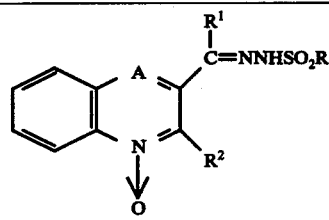

| | | | | IN VITRO | | | | IN VIVO vs. *Sal. Cholarasuis* at 25 mg./Kg.; % Survivors | |
|---|---|---|---|---|---|---|---|---|---|
| A | $R^1$ | $R^2$ | R | *Staph. aureus* | *E. Coli* | *Strep. pyogenes* | *Salmonella cholerasuis* | *Pasteurella multocida* | PO | SC |
| N→O | H | H | C$_6$H$_5$ | 100 | 12.5 | 25 | 12.5 | 12.5 | — | — |
| N→O | H | H | 4-CH$_3$C$_6$H$_4$ | 25 | 1.56 | 12.5 | 6.25 | 3.125 | 30 | 100 |
| N→O | H | H | 4-FC$_6$H$_4$ | 25 | 3.125 | 12.5 | 6.25 | 3.125 | 10 | 30 |
| N→O | H | H | CH$_3$ | 25 | 3.125 | 12.5 | 6.25 | 12.5 | 10 | 60 |
| N | H | H | 4-CH$_3$OC$_6$H$_4$ | 12.5 | 3.125 | 6.25 | 6.25 | 1.56 | — | — |
| N | H | H | 4-CH$_3$C$_6$H$_4$ | 25 | 3.125 | 12.5 | 3.125 | 3.125 | 60 | 100 |

The following examples are provided for the purpose of illustration only, and are not to be construed as limitations of the invention. The diagnostic absorption bands of infrared (IR) spectra are reported as wave numbers (cm$^{-1}$). Nuclear magnetic resonance spectra ($^1$H-nmr) are measured at 60 MHz for solutions in deuterotrifluoroacetic acid (CF$_3$CO$_2$D) or deuterochloroform (CDCl$_3$), and peak positions are expressed in parts per million downfield from tetramethylsilane. The following abbreviations for peak shapes are used: s, singlet; m, multiplet.

EXAMPLE 1

4-Oxoquinoxaline 2-Carboxaldehyde

A. 2-Hydroxymethyl-1,4-dioxoquinoxaline (1.00 g., 5.20 mmole) was added to 3 ml. of concentrated hydrochloric acid and the mixture was heated at 100° C. with stirring for 1 hour. The precipitated tan solid was collected by suction filtration and recrystallized from ace- A. 2-Methylcarbonyl-3-methyl-1,4-dioxoquinoxaline (20.0 g., 0.092 mole), prepared by condensing pentane-2,4-dione with benzofurazan-1-oxide in the presence of a catalytic amount of sodium hydroxide, was dissolved in 200 ml. of 1-propanol containing trimethyl phosphite (12.5 g., 0.101 mole). After heating at reflux for 4 hours, the reaction mixture was concentrated in vacuo causing a crystalline solid to form. This was collected by filtration and washed with ether to obtain 4.91 g. of product, M.P. 93°–94° C. An additional 6.51 g. was obtained in a second crop (total yield 63%). $^1$H-nmr (CDCl$_3$), ppm δ: 2.80 (6, s, CH$_3$, COCH$_3$), 7.82 (2, m, H at 6- and 7-positions), 8.15 (1, m, H at 8-position), 8.60 (1, m, H at 5-position); IR (KBr) cm$^{-1}$: 1710 (C = 0); uv λ$_{max}^{CH_3OH}$, nm: 253 (ε = 29,200), 325 (ε = 7,600).

The mass spectrum showed a molecular ion at M/e 202.

Analysis: Calc'd for $C_{11}H_{10}N_2O_2$: C, 65.41; H, 4.99; H, 13.87. Found: C, 65.14; H, 5.02; N, 13.94.

B. When the above procedure is repeated employing the appropriate 6-and/or 7-substituted-2-methylcarbonyl-3-methyl-1,4-dioxoquinoxaline in each case, the following compounds are similarly prepared.

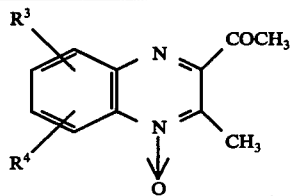

| $R^3$ | $R^4$ |
|---|---|
| Cl | H |
| $CH_3$ | H |
| $OCH_3$ | H |
| $SO_2NH_2$ | H |
| $SO_2NHCH_3$ | H |
| $SO_2N(CH_3)_2$ | H |
| Cl | Cl |
| $CH_3$ | $CH_3$ |

C. When the procedure of Example 2A is repeated but employing the appropriate 2-methylcarbonyl-1,4-dioxoquinoxaline in place of 2-methylcarbonyl-3-methyl-1,4-dioxoquinoxaline in each case, the following 4-oxoquinoxalines are obtained.

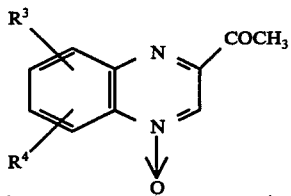

| $R^3$ | $R^4$ |
|---|---|
| H | H |
| Cl | H |
| $CH_3$ | H |
| $OCH_3$ | H |
| $SO_2NH_2$ | H |
| $SO_2NHCH_3$ | H |
| $SO_2N(CH_3)_2$ | H |
| Cl | Cl |
| $CH_3$ | $CH_3$ |

EXAMPLE 3

3-Methyl-4-oxoquinoxaline-2-carboxaldehyde

A. 2-Hydroxymethyl-3-methyl-1,4-dioxoquinoxaline (4.29 g., 20.8 mmole) was added in portions to 10 ml. of concentrated sulfuric acid with stirring at room temperature. The reaction is exothermic. The resulting dark reaction mixture was stirred at room temperature for 3 hours, then heated at 70° C. for 30 minutes, cooled and poured onto crushed ice. The precipitated solid material was removed by filtration and the filtrate extracted with several portions of chloroform. Evaporation of the dried chloroform extracts afforded a residue which was purified by column chromatography on silica gel. Elution with benzene gave an unidentified solid, 200 mg. Further elution with chloroform/ethyl acetate (1:1 by volume) gave 1.40 g. (35.8%) of the desired product which upon crystallization from a minimum volume of acetone melted at 167°-169° C. $^1$H-nmr (CDCl$_3$) ppm δ: 10.2 (s, 1, CHO), 8.65 (m, 1, H at 8-position), 8.30 (m, 1, H at 5-position), 7.90 (m, 2, H at 6- and 7-positions), 3.00 (s, 3, $CH_3$); IR (KBr) cm$^{-1}$: 2841, 1724 (C = 0). The mass spectrum showed a molecular ion at M/e 188.

Analysis: Calc'd for $C_{10}H_8N_2O_2$: C, 63.83; H, 4.25; N, 14.89. Found: C, 63.67; H, 4.45; N, 14.63.

B. When the appropriate 6- and/or 7-substituted 2-hydroxymethyl-3-methyl-1,4-dioxoquinoxaline is employed in the procedure of Example 2A, the following 4-oxoquinoxalines are obtained in each case.

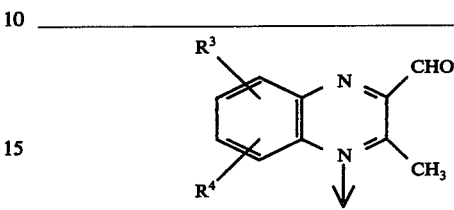

| $R^3$ | $R^4$ |
|---|---|
| Cl | H |
| $CH_3$ | H |
| $OCH_3$ | H |
| $SO_2NH_2$ | H |
| $SO_2NHCH_3$ | H |
| $SO_2N(CH_3)_2$ | H |
| Cl | Cl |
| $CH_3$ | $CH_3$ |

EXAMPLE 4

1,4-Dioxoquinoxaline-2-carboxaldehyde p-Toluenesulfonylhydrazone

A mixture of 1,4- dioxoquinoxaline-2-carboxaldehyde (1.90 g., 0.01 mole) and p-toluenesulfonylhydrazine (2.79 g., 0.015 mole) in 200 ml. of methyl alcohol was refluxed for 1 hour, cooled and the precipitated solid collected by filtration to give 3.48 g. (97% yield) of the title compound, M.P. 160° C. (dec.).

Analysis: Calc'd for $C_{16}H_{14}N_4O_4S$: C, 53.62; H, 3.94; N, 15.63. Found: C, 53.31; H, 4.00; N, 15.68.

EXAMPLE 5

1,4-Dioxoquinoxaline-2-carboxaldehyde Benzenesulfonylhydrazone

A mixture of 1,4-dioxoquinoxaline-2-carboxaldehyde (1.00 g., 0.0052 mole) and benzenesulfonylhydrazine (0.95 g., 0.0052 mole) in methanol (75 ml.) was stirred at room temperature for 2 hours. The yellow precipitate was collected by filtration and air dried to give 1.52 g. (83% yield) of the title compound, M.P. 147° C. (dec.).

EXAMPLE 6

When the procedures of Examples 4 or 5 were repeated, but employing the appropriate sulfonylhydrazine in each case, the following compounds were obtained.

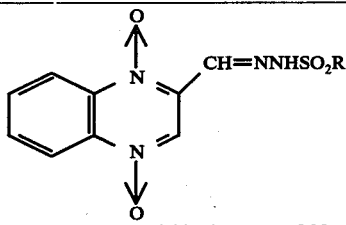

| R | Yield, % | M.P., ° C. |
|---|---|---|
| 4-FC$_6$H$_4$ | 49 | 144° (dec.) |
| $CH_3$ | 60 | 169° (dec.) |

-continued

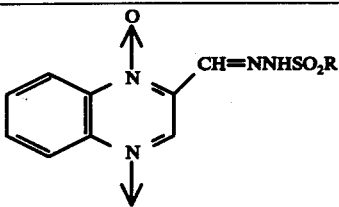

| R | Yield, % | M.P., °C. |
|---|---|---|
| 4-CH₃OC₆H₄ | 50 | >250° |

EXAMPLE 7

4-Oxoquinoxaline-2-carboxaldehyde p-Toluenesulfonylhydrazone

A mixture of 4-oxoquinoxaline-2-carboxaldehyde (0.95 g., 0.0057 mole) and p-toluenesulfonylhydrazine (2.10 g., 0.011 mole) in 100 ml. of methyl alcohol was stirred at room temperature for 1 hour. The solvent was removed by evaporation and the residue recrystallized from aqueous dimethylformamide to give 1.82 g. (98% yield) of the title compound, M.P. 160°-163° C. (dec.).

Analysis: Calc'd for $C_{16}H_{14}N_4O_3S$: C, 56.13; H, 4.12; N, 16.36. Found: C, 55.84; H, 4.35; N, 15.94.

EXAMPLE 8

4-Oxoquinoxaline-2-carboxaldehyde p-Methoxybenzenesulfonylhydrazone

A mixture of 4-oxoquinoxaline-2-carboxaldehyde (0.87 g., 0.005 mole) and p-methoxybenzenesulfonylhydrazine (1.15 g., 0.056 mole) in 90 ml. of methanol was stirred at room temperature for 2 hours. The precipitate was filtered and recrystallized from methanol to afford 1.20 g. (66% yield) of product, M.P. 190°-191° C. (dec.).

EXAMPLE 9

The following 4-oxoquinoxaline-2-carboxaldehyde sulfonylhydrazones were similarly prepared by the procedure of Example 8.

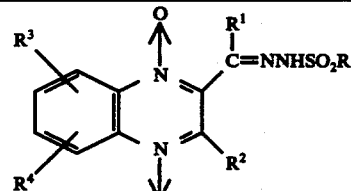

| R | Yield, % | M.P., °C. |
|---|---|---|
| C₆H₅ | 70 | 133° (dec.) |
| 4-FC₆H₄ | 78 | 123° (dec.) |
| CH₃ | 21 | 140-1° (dec.) |

EXAMPLE 10

2-Methylcarbonyl-3-methyl-4-oxoquinoxaline p-Toluenesulfonylhydrazone

A solution of 2-methylcarbonyl-3-methyl-4-oxoquinoxaline (1.70 g., 8.4 mmoles) and p-toluenesulfonylhydrazine (3.10 g., 16.5 mmoles) in 50 ml. of methanol was heated on the steam bath for 30 minutes, cooled and concentrated to 25 ml. volume. The precipitated product was collected by suction filtration to afford 2.53 g. (81%) of the title compound, M.P. 190°-192° C. (dec.).

EXAMPLE 11

3-Methyl-4-oxoquinoxaline-2-carboxaldehyde p-Toluenesulfonylhydrazone

A solution of 3-methyl-4-oxoquinoxaline-2-carboxaldehyde (0.74 g., 3.9 mmoles) and p-toluenesulfonylhydrazine (1.48 g., 7.9 mmoles) in 25 ml. of methanol was heated on a steam bath for 30 minutes. The precipitate was filtered to give the desired product, 1.10 g. (78%), M.P. 146°-148° C.

Analysis: Calc'd for $C_{17}H_{16}N_4O_3S$: C, 57.29; H, 4.52; N, 15.72. Found: C, 57.48; H, 4.62; N, 15.92.

EXAMPLE 12

By employing the above procedures and the appropriate starting materials in each case, the following 1,4-dioxoquinoxalines are obtained.

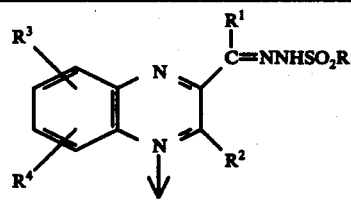

| R | R¹ | R² | R³ | R⁴ |
|---|---|---|---|---|
| (CH₃)₂CHCH₂CH₂ | H | H | H | H |
| 2-naphthyl | H | H | H | H |
| CF₃ | CH₃ | H | H | H |
| CH₃CH₂— | CH₃ | CH₃ | H | H |
| C₆H₅CH₂— | H | CH₃ | H | H |
| C₆H₅CH=CH— | H | H | CH₃ | H |
| 4-ClC₆H₄— | H | H | CH₃ | CH₃ |
| 3-BrC₆H₄— | H | H | Cl | H |
| 2-NO₂C₆H₄— | H | H | Cl | Cl |
| 4-Cl-3-NO₂C₆H₃— | CH₃ | CH₃ | CH₃O | H |
| 2,5-Cl₂C₆H₃— | H | H | SO₂NH₂ | H |
| 2,4-(CH₃)₂C₆H₃— | H | H | SO₂NHCH₃ | H |
| 2,4-(NO₂)₂C₆H₃— | H | CH₃ | SO₂N(CH₃)₂ | H |
| CF₃ | H | H | CH₃O | H |
| CH₃ | CH₃ | CH₃ | CH₃ | CH₃ |
| 4-CH₃OC₆H₄— | CH₃ | CH₃ | Cl | Cl |
| 1-naphthyl | CH₃ | H | Cl | H |
| 2-CH₃OC₆H₄— | CH₃ | H | CH₃ | CH₃ |

EXAMPLE 13

By employing the above procedures and the appropriate starting material in each case, the following 4-oxoquinoxalines are similarly obtained.

| R | R¹ | R² | R³ | R⁴ |
|---|---|---|---|---|
| CH₃(CH₂)₃CH₂— | H | CH₃ | Cl | H |
| (CH₃)₂CH— | H | H | Cl | Cl |
| 2-naphthyl | H | CH₃ | CH₃ | H |
| CF₃ | H | CH₃ | CH₃ | CH₃ |
| C₆H₅CH₂— | H | H | CH₃O | H |
| C₆H₅CH=CH— | CH₃ | CH₃ | SO₂NH₂ | H |
| 2-ClC₆H₄— | CH₃ | H | SO₂NHCH₃ | H |
| 4-BrC₆H₄— | CH₃ | H | SO₂N(CH₃)₂ | H |
| 4-Cl-3-NO₂C₆H₃— | H | H | CH₃O | H |
| 2,5-Cl₂C₆H₃— | CH₃ | H | CH₃ | CH₃ |

-continued $$\begin{array}{c} R^3 \\ \diagdown \\ R^4 \end{array} \diagup \begin{array}{c} N \\ \diagdown \\ N \\ \downarrow \\ O \end{array} \diagup \begin{array}{c} R^1 \\ | \\ C{=}NNHSO_2R \\ R^2 \end{array}$$

| R | R¹ | R² | R³ | R⁴ |
|---|---|---|---|---|
| 2,4-(CH₃O)₂C₆H₃— | CH₃ | H | H | H |
| 2,4-(NO₂)₂C₆H₃— | CH₃ | H | H | H |
| 1-naphthyl | H | H | H | H |
| 2-CH₃OC₆H₄— | CH₃ | CH₃ | CH₃ | CH₃ |

EXAMPLE 14

4-Oxoquinoxaline-2-carboxaldehyde Hydrazone

A solution of 4-oxoquinoxaline-2-carboxaldehyde (1.10 g., 0.063 mole) in anhydrous ethanol (50 ml.) was treated with hydrazine hydrate (2 ml.) and the resulting solution heated at reflux for 30 minutes. Filtration of the cooled reaction mixture and recrystallization from ethanol afforded 647 mg. (55%) of product, M.P. 189°–191° C. (dec.).

Analysis: Calc'd. for C₉H₈ON₄: C, 57.45; H, 4.26; N, 29.79 Found: C, 56.96; H, 4.37; N, 29.35.

EXAMPLE 15

4-Oxoquinoxaline-2-carboxaldehyde-p-methoxybenzenesulfonylhydrazone

A solution of 4-oxoquinoxaline-2-carboxaldehyde hydrazone (0.768 g., 0.004 mole), p-methoxybenzenesulfonylchloride (0.841 g., 0.004 mole) and triethylamine (0.6 ml., 0.004 mole) in tetrahydrofuran (60 ml.) was stirred at room temperature for 2 hours, then filtered. The product was recrystallized from methanol to give 0.996 g. (66%) of the title compound, M.P. 190°–191° C. (dec.).

EXAMPLE 16

Employing the appropriate starting materials in each case the following 1,4-dioxo- and 4-oxoquinoxalinesulfonylhydrazones are prepared by the procedures of Examples 14 and 15.

$$\begin{array}{c} R^3 \\ \diagdown \\ R^4 \end{array} \diagup \begin{array}{c} A \\ \diagdown \\ N \\ \downarrow \\ O \end{array} \diagup \begin{array}{c} R^1 \\ | \\ C{=}NNHSO_2R \\ R^2 \end{array}$$

| A | R | R¹ | R² | R³ | R⁴ |
|---|---|---|---|---|---|
| N | CH₃CH₂— | CH₃ | CH₃ | H | H |
| N | (CH₃)₂CHCH₂— | H | CH₃ | H | H |
| N | CF₃— | H | H | CH₃ | CH₃ |
| N | C₆H₅— | CH₃ | H | Cl | Cl |
| N | 1-naphthyl | H | H | SO₂N(CH₃)₂ | H |
| N | C₆H₅CH₂— | CH₃ | CH₃ | CH₃O | H |
| N → O | C₆H₅CH═CH— | H | CH₃ | SO₂NH₂ | H |
| N → O | 2-BrC₆H₄— | CH₃ | CH₃ | SO₂NHCH₃ | H |
| N → O | 4-Cl-3-NO₂C₆H₃— | H | H | Cl | H |
| N → O | 2,4-(CH₃)₂C₆H₃— | H | CH₃ | Cl | Cl |
| N → O | 2,4-(CH₃O)₂C₆H₃— | H | H | H | H |

EXAMPLE 17

1,4-Dioxoquinoxaline-2-carboxaldehyde p-Toluenesulfonylhydrazone

To a solution containing 1,4-dioxoquinoxaline-2-carboxaldehyde dimethylacetal prepared by the method of British Pat. No. 1,215,815, (11.8 g., 0.05 mole), p-toluenesulfonylhydrazine (10.4 g., 0.056 mole) and acetic acid (140 ml.) is added 4.0 ml. of concentrated hydrochloric acid. The resulting mixture is heated on a steam bath for approximately 20–30 minutes then allowed to stir overnight at room temperature. The precipitated product is isolated by filtration and dried.

By employing the appropriate starting materials in the above procedure the following 1,4-dioxo- and 4-oxoquinoxalinesulfonylhydrazones are similarly prepared.

$$\begin{array}{c} R^3 \\ \diagdown \\ R^4 \end{array} \diagup \begin{array}{c} A \\ \diagdown \\ N \\ \downarrow \\ O \end{array} \diagup \begin{array}{c} R^1 \\ | \\ C{=}NNHSO_2R \\ R^2 \end{array}$$

| A | R | R¹ | R² | R³ | R⁴ |
|---|---|---|---|---|---|
| N → O | CH₃ | H | H | H | H |
| N → O | CH₃(CH₂)₃CH₂— | H | CH₃ | H | H |
| N → O | CF₃— | CH₃ | CH₃ | CH₃ | CH₃ |
| N → O | C₆H₅— | H | H | Cl | Cl |
| N → O | 2-naphthyl | H | CH₃ | CH₃O | H |
| N → O | C₆H₅CH₂— | H | H | SO₂NH₂ | H |
| N | C₆H₅CH═CH— | H | H | SO₂NHCH₃ | H |
| N | 4-ClC₆H₄— | CH₃ | H | SO₂N(CH₃)₂ | H |
| N | 2,4-(NO₂)₂C₆H₃— | CH₃ | CH₃ | Cl | H |
| N | 2,4-Br₂C₆H₃— | H | H | H | H |
| N | 2-CH₃OC₆H₄— | H | H | CH₃O | H |

EXAMPLE 18

The standard, nutritionally balanced rations of broiler chicks and turkey poults are supplemented as shown in the following table:

| Supplemental Compound | Supplementation, grams/ton of feed |
|---|---|
| 1,4-Dioxoquinoxaline-2-carboxaldehyde p-toluenesulfonylhydrazone | 5 |
|  | 50 |
|  | 100 |
|  | 150 |
| 4-Oxoquinoxaline-2-carboxaldehyde p-toluenesulfonylhydrazone | 5 |
|  | 50 |
|  | 100 |
|  | 150 |

When chicks and poults are fed the supplemented ration and compared with control birds fed an unsupplemented diet, the supplemented rations in each case are found to bring about economically significant gains in growth and feed efficiency.

For this study, the experimental birds, the supplemented and control rations are assigned pens in accordance to randomized block designs. Each observation is an average of about six pen replicates, each pen containing about 10 birds. The experiments are conducted in battery brooders for from 1 to 28 days of bird age.

EXAMPLE 19

In further tests the compounds of Examples 4 to 11 are added to the standard nutritionally balanced animal feed compositions normally given to swine, sheep, steers, goats, dogs and mink at levels of from 5 to 200 g. per ton of feed. When compared with control animals of each species maintained on unsupplemented feed, the animals receiving the supplemented diets are observed to undergo accelerated growth with improved feed efficiency.

PREPARATION A

6(or 7)-Substituted and 6,7-Disubstituted-1,4-dioxoquinoxaline-2-carboxaldehydes Pyrrolidine (0.05 M) is added with stirring to a mixture of the appropriate benzofuroxan (0.1 M), pyruvaldehyde dimethylacetal (0.1 M) and acetonitrile (100 ml.). The mixture is allowed to stand overnight at room temperature and is then evaporated to dryness in vacuo. The residue is taken up in concentrated hydrochloric acid (25 ml.), the mixture diluted with water and then extracted with chloroform. The extract is dried ($Na_2SO_4$) and stripped of chloroform to give the desired product which is used as is or, if desired, is purified by crystallization from an appropriate solvent system; e.g., chloroform-hexane.

The following compounds are thus prepared:

| $R^3$ | $R^4$ |
|---|---|
| H | H |
| Cl | H |
| $CH_3$ | H |
| $SO_2NH_2$ | H |
| $SO_2NHCH_3$ | H |
| $SO_2N(CH_3)_2$ | H |
| $OCH_3$ | H |
| Cl | Cl |
| $CH_3$ | $CH_3$ |

PREPARATION B

2-Hydroxymethyl-1,4-dioxoquinoxaline i. 1,4-Dioxoquinoxaline-2-carboxaldehyde (1.90 g., 10 mmoles) was dissolved in 30 ml. of 1-propanol containing trimethyl phosphite (1.24 g., 10 mmoles). The mixture was heated at reflux for 30 minutes, then cooled to 15° C. to afford a yellow precipitate which was collected by suction filtration and washed with methanol to yield 0.64 g. (33%) of title compound, M.P. 176°–178° C. $^1$H-nmr ($CF_3CO_2D$), ppm δ: 5.47 (2, s, $CH_2$), 8.28 (2, m, H at 6- and 7-positions), 8.85 (2, m, H at 5- and 8-positions), 9.37 (1, s, H at 3-position); IR (KBr), $cm^{-1}$: 3220 (OH); ultraviolet spectrum, $\lambda_{max}^{MeOH}$, nm: 232 (ε=18,270), 259 (ε=22,880), 379 (ε=12,980). The mass spectrum showed a molecular ion at M/e 192.

ii. 1,4-Dioxoquinoxaline-2-carboxaldehyde (1.90 g., 10 mmoles) was suspended in 100 ml. of methanol. Sodium borohydride (0.095 g., 2.5 mmoles) was added in small portions over about 1 minute and the reaction mixture was then stirred for 30 minutes at room temperature, during which time a yellow solid precipitated. The solid was collected by suction filtration and washed with ether to obtain 1.50 g. (78%) of the title compound, M.P. 180°–182° C. The nmr, infrared, ultraviolet and mass spectra were identical to those obtained with the material from procedure i above. An analytical sample was obtained by recrystallization from methanol, M.P. 214°–215° C.

Analysis: Calc'd for $C_9H_8N_2O_3$: C, 56.30; H, 4.20; N, 14.59. Found: C, 56.28; H, 4.26; N, 14.89.

iii. Employing the appropriate product of Preparation A as starting material in the above procedures, the following 6(or 7)-substituted and 6,7-disubstituted-2-hydroxymethyl-1,4-dioxoquinoxalines are prepared.

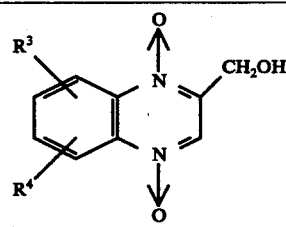

| $R^3$ | $R^4$ |
|---|---|
| Cl | H |
| $CH_3$ | H |
| $OCH_3$ | H |
| $SO_2NH_2$ | H |
| $SO_2NHCH_3$ | H |
| $SO_2N(CH_3)_2$ | H |
| Cl | Cl |
| $CH_3$ | $CH_3$ |

PREPARATION C

2-Methylcarbonyl-3-methyl-1,4-dioxoquinoxaline

1. Pentane-2,4-dione (180 g., 1.80 mole) and benzofuroxan (204 g., 1.50 mole) were added to 1000 ml. of ethanol containing a catalytic amount (6.0 g., 0.15 mole) of sodium hydroxide. The reaction was exothermic and was maintained at 55° C. by means of an ice-bath for 30 minutes. The reaction mixture was then stirred overnight at room temperature. The precipitated yellow solid was collected by filtration, washed with ethanol and dried to afford 176 g. of product (54%), M.P. 154°–155° C. $^1$H-nmr ($CDCl_3$) ppm δ: 2.50 (3, s, $CH_3$ or $COCH_3$), 2.72 (3, s, $COCH_3$ or $CH_3$), 7.85 (2, m, H at 6- and 7-positions), 8.52 (2, m, H at 5- and 8-positions); IR (KBr), $cm^{-1}$: 1725 (C=O); ultraviolet spectrum, $\lambda_{max}^{CH_3OH}$, nm: 235 (ε= 20,600), 263 (ε=19,700), 384 (ε=10,860). The mass spectrum showed a molecular ion at M/e 218.

Analysis: Calc'd for $C_{11}H_{10}N_2O_3$: C, 60.61; H, 4.62; N, 12.85. Found: C, 60.45; H, 4.67; N, 12.87.

ii. By employing the appropriate benzofuroxan in the above procedure the following 6(or 7)-substituted and 6,7-disubstituted-2-methylcarbonyl-3-methyl-1,4-dioxoquinoxalines are obtained.

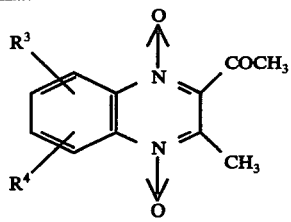

| R³ | R⁴ |
|---|---|
| Cl | H |
| CH₃ | H |
| OCH₃ | H |
| SO₂NH₂ | H |
| SO₂NHCH₃ | H |
| SO₂N(CH₃)₂ | H |
| Cl | Cl |
| CH₃ | CH₃ |

PREPARATION D

2-Methylcarbonyl-1,4-dioxoquinoxalines

Employing an equivalent amount of biacetyl in place of pentane-2,4-dione and the appropriate benzofuroxan in the procedure of Preparation C, the following compounds are similarly obtained.

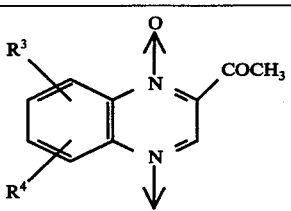

| R³ | R⁴ |
|---|---|
| H | H |
| Cl | H |
| CH₃ | H |
| OCH₃ | H |
| SO₂NH₂ | H |
| SO₂NHCH₃ | H |
| SO₂N(CH₃)₂ | H |
| Cl | Cl |
| CH₃ | CH₃ |

PREPARATION E

6(or 7)-Substituted and 6,7-Disubstituted-2-hydroxymethyl-3-methyl-1,4-dioxoquinoxalines A mixture of the appropriate 5- or 5,6-substituted-benzofuroxan (0.1M), 4-hydroxy-2-butanone (0.15 M), pyrrolidine (0.025 M) and N,N-dimethylformamide (20 ml.) is stirred at room temperature for 3 hours. The solid which precipitates is filtered off, washed with acetonitrile and dried to provide the product. (If the product does not precipitate, the reaction mixture is evaporated under reduced pressure and the residue triturated under ether.)

The following compounds are thus prepared:

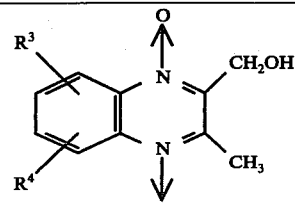

| R³ | R⁴ |
|---|---|
| H | H |
| Cl | H |
| CH₃ | H |
| OCH₃ | H |
| SO₂NH₂ | H |
| SO₂NH(CH₃) | H |
| SO₂N(CH₃)₂ | H |
| Cl | Cl |
| CH₃ | CH₃ |

PREPARATION F

6(or 7)-Substituted and 6,7-Disubstituted-2-bromomethyl-3-methyl-1,4-dioxoquinoxalines A solution of the appropriate 6(or 7)-substituted or 6,7-disubstituted 2-hydroxymethyl-3-methyl-1,4-dioxoquinoxaline (0.1 M) and 48% aqueous hydrobromic acid (150 ml.) is warmed to 90° C. After an hour the solution is allowed to cool to room temperature, and is evaporated under reduced pressure to furnish the essentially pure 6(or 7)-substituted or 6,7-disubstituted-2-bromomethyl-3-methylquinoxaline-1,4-dioxide which is used without further purification. In certain cases the product crystallizes directly from the reaction solution. If the substituted 3-methyl-2-quinoxalinemethanol-1,4-dioxide does not form a solution with 48% aqueous hydrobromic acid, solution is obtained by using 30% hydrogen bromide in acetic acid.

PREPARATION G

6(or 7)-Substituted and 6,7-Disubstituted-3-Methyl-1,4-dioxoquinoxaline-2-carboxaldehydes A suspension of the appropriate 6(or 7)-substituted or 6,7-disubstituted 2-bromomethyl-3-methyl-1,4-dioxoquinoxaline (0.1 M), acetonitrile (200 ml.) and dimethylsulfoxide (50 ml.) is heated under reflux for 30 minutes. Dimethylsulfide evolves. After the reaction subsides, the mixture is cooled to room temperature and the aldehyde product filtered. It is used without further purification.

The compounds listed below are prepared in this manner.

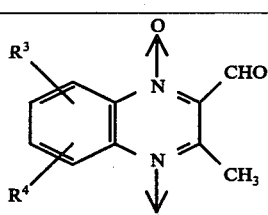

| R³ | R⁴ |
|---|---|
| H | H |
| Cl | H |
| CH₃ | H |
| OCH₃ | H |

-continued

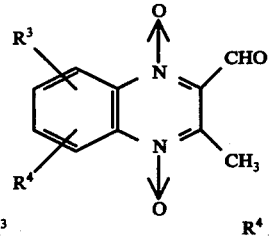

| $R^3$ | $R^4$ |
|---|---|
| $SO_2NH_2$ | H |
| $SO_2NH(CH_3)$ | H |
| $SO_2N(CH_3)_2$ | H |
| Cl | Cl |
| $CH_3$ | $CH_3$ |

What is claimed is:

1. A compound of the formula

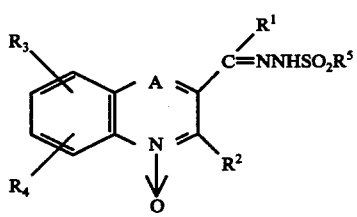

wherein A is N; $R^1$, $R^2$, $R^3$ and $R^4$ are each hydrogen; and $R^5$ is a member selected from the group consisting of methylphenyl and methoxyphenyl.

2. A compound of the formula

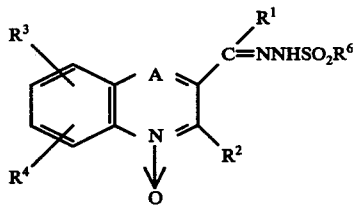

wherein A is N→O; $R^1$, $R^2$, $R^3$ and $R^4$ are each hydrogen; and $R^6$ is a member selected from the group consisting of alkyl having from one to five carbon atoms, phenyl, methylphenyl and fluorophenyl.

3. The compound according to claim 1 wherein $R^5$ is 4-methylphenyl.

4. The compound according to claim 1 wherein $R^5$ is 4-methoxyphenyl.

5. The compound according to claim 2 wherein $R^6$ is methyl.

6. The compound according to claim 2 wherein $R^6$ is phenyl.

7. The compound according to claim 2 wherein $R^6$ is 4-methylphenyl.

8. The compound according to claim 2 wherein $R^6$ is 4-fluorophenyl.

9. A method for promoting growth and improving feed efficiency of animals which comprises feeding said animal a growth promoting and feed efficiency improving amount of a compound of the formula

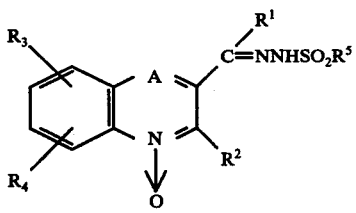

wherein A is N; $R^1$, $R^2$, $R^3$ and $R^4$ are each hydrogen; and $R^5$ is a member selected from the group consisting of methylphenyl and methoxyphenyl.

10. A method for promoting growth and improving feed efficiency of animals which comprises feeding said animals a growth promoting and feed efficiency improving amount of a compound of the formula

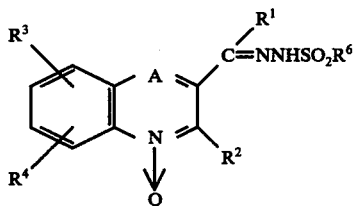

wherein A is N→O; $R^1$, $R^2$, $R^3$ and $R^4$ are each hydrogen; and $R^6$ is a member selected from the group consisting of alkyl having from one to five carbon atoms, phenyl, methylphenyl and fluorophenyl.

11. The method according to claim 9 wherein $R^5$ is 4-methylphenyl.

12. The method according to claim 10 wherein $R^6$ is 4-methylphenyl.

13. An animal feed composition which comprises a nutritionally balanced animal feed containing from about 5 g. to about 200 g. per ton of a compound of claim 1.

14. An animal feed composition which comprises a nutritionally balanced animal feed containing from about 5 g. to 200 g. per ton of a compound of claim 2.

* * * * *